United States Patent [19]
Berezin et al.

[11] Patent Number: 5,649,169
[45] Date of Patent: Jul. 15, 1997

[54] METHOD AND SYSTEM FOR DECLUSTERING SEMICONDUCTOR DEFECT DATA

[75] Inventors: Alan Berezin; Reuben Quintanilla, both of Austin, Tex.

[73] Assignee: Advanced Micro Devices, Inc., Sunnyvale, Calif.

[21] Appl. No.: 492,803

[22] Filed: Jun. 20, 1995

[51] Int. Cl.$^6$ ................................. H01L 29/38
[52] U.S. Cl. .................. 395/500; 364/468.17; 437/939
[58] Field of Search .................. 395/500; 324/158 R, 324/62; 437/8, 939; 250/572; 382/8, 147, 149; 371/22.1; 364/468.17, 468.28

[56] References Cited

U.S. PATENT DOCUMENTS

| | | | |
|---|---|---|---|
| 3,751,647 | 8/1973 | Maeder et al. | 235/151.11 |
| 3,983,479 | 9/1976 | Lee et al. | 324/158 R |
| 4,100,486 | 7/1978 | Casowitz et al. | 324/62 |
| 4,579,455 | 4/1986 | Levy et al. | 356/394 |
| 4,855,523 | 8/1989 | Weber | 437/8 |
| 5,032,734 | 7/1991 | Orazio, Jr. et al. | 250/572 |
| 5,129,009 | 7/1992 | Lebeau | 382/8 |
| 5,256,578 | 10/1993 | Corley et al. | 437/8 |
| 5,274,434 | 12/1993 | Morioka et al. | 356/237 |
| 5,317,380 | 5/1994 | Allemand | 356/338 |
| 5,440,649 | 8/1995 | Kiyasu et al. | 382/147 |
| 5,539,752 | 7/1996 | Berezin et al. | 371/22.1 |

OTHER PUBLICATIONS

"Framework for a Defect Reduction Program", by B. Duffy et al., 1990 IEEE/SEMI Advanced Semiconductor Manufacturing Conference, pp. 77–81.

"Fast Turn Around Post Process Yield Enchancement for Custom VLSI Foundries", by H. Parks, 1990 IEEE/SEMI Advanced Semiconductor Manufacturing Conference, pp. 82–87.

*Primary Examiner*—Kevin J. Teska
*Assistant Examiner*—Russell W. Frejd
*Attorney, Agent, or Firm*—Haynes and Boone, L.L.P.

[57] ABSTRACT

Method and system for declustering semiconductor defect data in cooperation with wafer scanning tools. Classification codes are assigned to defect data stored in wafer scan records by first determining the local density of the defects within a preselected area of the wafer substrate and by determining the average density of all of the defects on the substrate. A search area is defined around a defect of interest, the search area having a radius proportional to the ratio of the local density to the average density. The defects are marked within the search area, and for each marked defect, a new search area is defined and additional defects are marked. At least one of the marked defects is then assigned with a "cluster" classification code and the remaining defects within the search areas are assigned with a "discardable" classification code. By increasing the search radius linearly as the density ratio increases, the system automatically and more accurately removes noise in defect data caused by wafer scratches and other defect clusters.

33 Claims, 7 Drawing Sheets

METHOD AND SYSTEM FOR DECLUSTERING SEMICONDUCTOR DEFECT DATA

TECHNICAL FIELD

The invention relates generally to the manufacture of semiconductor integrated circuit ("IC") chips and, more particularly, to a method and system for performing in-line spacial map analysis of semiconductor wafer defects to more accurately decluster defect data.

BACKGROUND OF THE INVENTION

The fabrication of semiconductor integrated circuits, or chips as they are commonly known, is an extremely complex process that involves several hundred or more operations. They are fabricated by selectively implanting impurities into, and applying conductive and insulative layers onto, a semiconductor substrate. Semiconductor chips are not manufactured individually, but rather as an assembly of a hundred or more chips on a "wafer," which is then diced up to produce the individual chips.

An ongoing problem in the manufacture of semiconductor chips has to do with yield. Because of various defects that can occur in fabrication of a wafer, significant numbers of wafer die have to be discarded for one reason or another, thereby decreasing the percentage yield per wafer and driving up the cost of individual chips. Defects are typically caused by foreign particles, minute scratches and other imperfections introduced during photoresist, photomask and diffusion operations. Yield impacts the number of wafer starts at the inception of production needed to meet specific customer order quantities for finished chips at the end of the production line. With the high demand for semiconductor chips and more orders than can possibly be filled by a fabrication facility, predicting yield to accurately gauge wafer starts, and utilizing defect information to remove yield detracting operations, are important aspects of improving the efficiency, and hence output, of the fabrication facility.

Wafer scanning tools are utilized to identify defects that occur in the chip manufacturing process for the aforementioned purposes. Typically, such tools are located at a variety of positions along the production line and comprise automated-vision inspection stations for identifying visual irregularities in the wafer die as they move through the line. The irregularities, i.e., defects, are recorded according to their coordinates, estimate of size or other parameters and are stored as records in a database. The records represent raw information that must then be analyzed or otherwise processed off line to determine the impact, if any, of the identified defects on product yield. Some defects, for example, do not adversely affect yield as much as others, and therefore must be classified differently for analysis purposes.

Commercially available wafer scanning tools include those made by KLA Instruments Corporation of Santa Clara, Calif., Tencor Instruments Corporation of Mountain View, Calif., Inspex, Inc. of Billerica, Mass. and numerous other manufacturers. Despite significant advances made in wafer scanning technology, the various tools that are available suffer striking deficiencies. In particular, such tools lack the capability to perform advanced classification and analysis of defect information necessary to accurately determine the true impact of wafer defects on yield. While conventional tools offer simple data presentation capabilities, such as the display of wafer maps, histograms and charts, they do not adequately classify or process the defect data. Classification codes must typically be manually entered into wafer scan records indicating the type of defect and its potential impact on yield. This is done by placing the wafer on a review station where a user makes a judgment as to what the defect identified by the scan tool is, enters a classification code in the record for that defect, then proceeds to the next defect.

More sophisticated tools perform limited automatic classification of defect records according to the location of the defect on the wafer, in an effort to remove consideration of defects that do not require any classification. For example, it is recognized that a number of defect points in close proximity to one another, collectively referred to as a "cluster," can indicate a single event such as a contaminant or scratch present across one or more die. The sometimes thousands of defect points comprising a cluster therefore inordinately skew the data, representing "noise" that should be treated as a smaller number of defects for yield determination purposes. Therefore, some tools include the ability to automatically "decluster" the defect data, i.e., convert a cluster containing potentially many defect points to a single or smaller number of defects. Unfortunately, however, decluster algorithms typically used with known tools are inaccurate in their ability to properly detect the presence of individual clusters on a densely defective wafer, or likewise the presence of a single cluster across multiple die. They also tend to be specific to a particular scan tool and are not readily adaptable for use with other tools.

Consequently, there is a need for a method and system that permits more accurate defect analysis to be performed in cooperation with semiconductor wafer scanning tools and, particularly, a method and system that declusters defect data in a way that better reflects conditions actually occurring on a wafer.

SUMMARY OF THE INVENTION

The present invention, accordingly, provides a method and a system for performing semiconductor manufacturing defect analysis in cooperation with wafer scanning tools that overcome or reduce disadvantages and limitations associated with prior methods and systems, particularly with respect to the declustering of defect data.

One aspect of the invention is a method for assigning classification codes to data associated with defects or other points on a substrate, such as a semiconductor wafer. The method comprises determining the local density of the points within a preselected area of the substrate and determining the average density of all of the points on said substrate. A search area having a radius proportional to the ratio of the local density to the average density is defined around a point of interest. Points located within the search area are then marked. For each marked point, a new search area is defined around the marked point, the new search area having a radius proportional to the ratio of the local density to said average density, additional points are marked within the new search area, and the process of defining new search areas and marking additional points within the new search areas is repeated until no further points are marked. At least one of the marked points is then assigned with a "cluster" classification code and the remaining points within the search areas are assigned with a "discardable" classification code.

In another aspect, the radius of the search area is set at a minimum radius for density ratios of less than a preselected value, and thereafter the search radius linearly increases as the density ratio increases. The search radius is set at a maximum radius for density ratios of greater than a preselected value.

In another aspect, the substrate has multiple die and cluster classification codes are assigned to marked points on each of the separate die.

In a preferred embodiment the invention is implemented as a computer program stored on a computer-readable medium. The program is run on a system compatible with a commercially available wafer scanning tool or on the scanning tool itself.

A technical advantage achieved with the invention is that it automatically and more accurately declusters, i.e., removes "noise" in defect data, caused by wafer scratches and other defects.

Another advantage achieved with the invention is that by declustering data at the die level, estimation of yield can be performed for any die on a wafer, as contrasted with yield estimation performed only for the entire wafer or lot.

BRIEF DESCRIPTION OF THE DRAWINGS

FIG. 4b is an enlarged, schematic diagram of the substrate of FIG. 4a.

DESCRIPTION OF THE PREFERRED EMBODIMENTS

Figure 1:
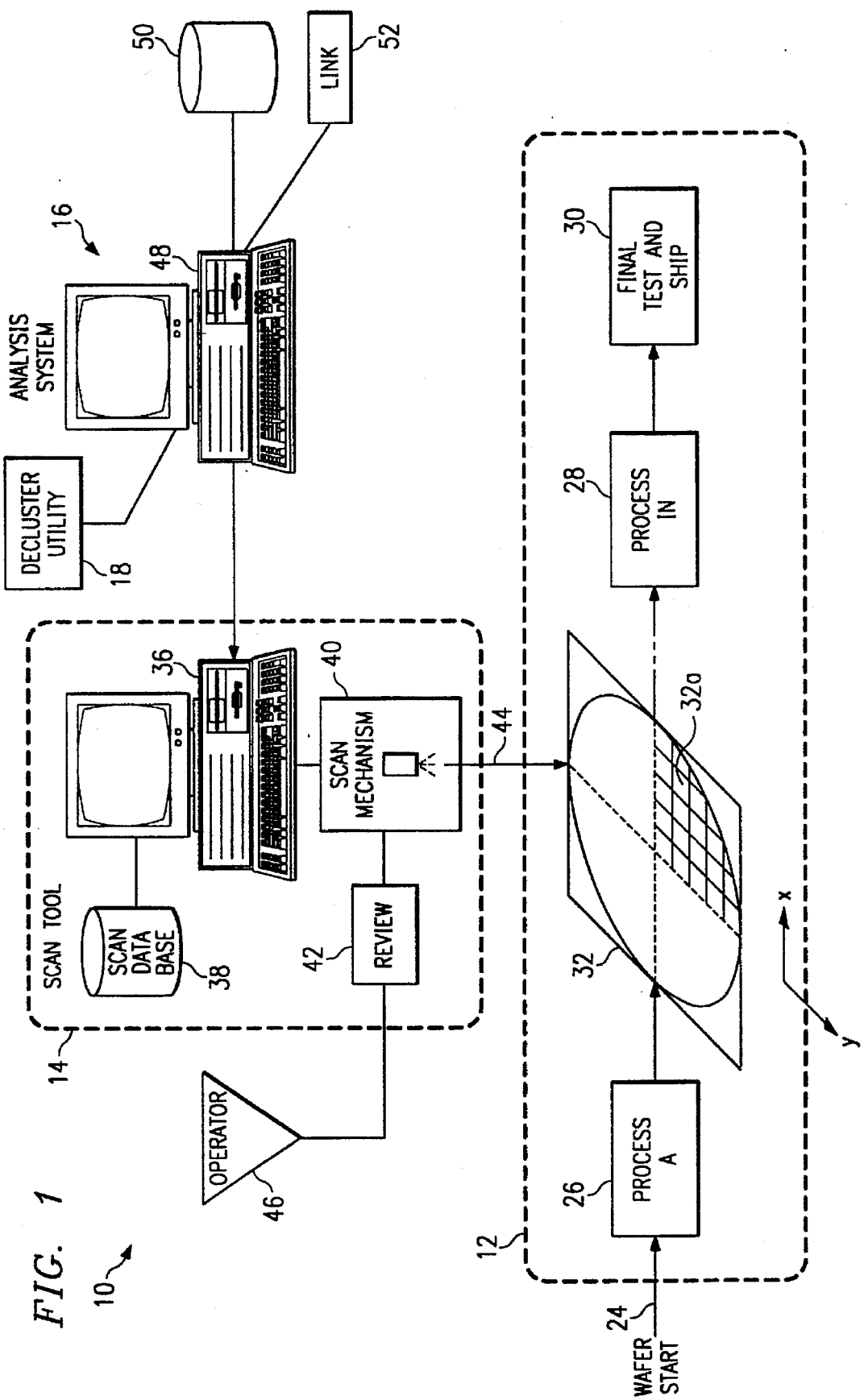
FIG. 1 is a schematic block diagram of a defect analysis system of the present invention for use with a wafer scanning tool in a semiconductor fabrication line.

In FIG. 1, the reference numeral 10 refers to an environment that is a portion of a semiconductor wafer fabrication facility ("wafer fab") for practicing the preferred embodiment of the invention. The environment 10 includes a manufacturing line 12 for fabricating semiconductor integrated circuit (IC) products, a scan tool 14 for visually inspecting wafers comprising the ICs at various stages of fabrication, and a defect analysis system 16 operatively coupled to the tool 14 for performing defect data decluster operations of the preferred embodiment, as discussed more fully below.

Operatively coupled to the system 16 is a computer program decluster utility 18 that performs the defect data decluster functions of the preferred embodiment, described fully below.

In the environment 10, semiconductor wafers are started in the manufacturing process, as indicated at line 24. The wafers are grouped and started in multiples, referred to as "lots", upon which a sequence of individual process operations are then performed. Process step A is first performed on a wafer lot as indicated by block 26. Subsequently, additional process steps are performed. Each process step, for example, comprises operations to be performed for a particular mask or layer of the wafers in the lot. Since the process steps are conventional and vary depending on the integrated circuit (IC) product being manufactured, they are not described in further detail. Block 28 represents completion of a sequence of many (up to N) processes, it being understood that in the typical wafer fab over one thousand processes, averaging up to a hundred or more steps each, must be completed. Upon completion, at block 30 the ICs comprising the wafers are ready for final test and shipment.

Following completion of Process A in block 26, the wafer scan tool 14 is used to perform a visual inspection of at least representative samples of the partially fabricated ICs in the wafer lot, as is represented by a wafer 32 located in proximity to the tool 14. While not shown, it is understood that similar inspections are performed at various stages of manufacturing of the wafer 32 and numerous tools 14 may be required to perform the inspections. Generally, the visual inspection performed by the scan tool 14 is used to identify defects of particular types to be used in an analysis of the effect of each defect type on the yield of the lot, or on the yield of individual wafers or wafer die in the lot. Engineering analysis of the process steps associated with particular defects may then be performed to identify and correct yield detracting operations.

The scan tool 14 comprises commercially available components and includes a computer 36, a database 38, a scan mechanism 40 and a review station 42. In a preferred embodiment, for example, the tool 14 is a KLA 21(xx) series defect scanning tool available from KLA Instruments Corporation. The scan mechanism 40 includes a microscope or other device for inspecting particles or other defects on the surface of the wafer 32. The wafer 32 may be moved relative to scan mechanism 40 by a transport mechanism (not shown) in the x and y directions perpendicular to the scan mechanism 40 to cause the microscopeto sweep over the surface of the wafer in a series of adjacent, possibly overlapping, scan lines. Each wafer die, such as a die 32a, is scanned and the information derived therefrom is converted to digital form and processed by the computer 36. In operation the scan mechanism 40 compares one die of the wafer 32 to the next. Presumably, every die will be identical to the next and any differences indicate an error, i.e., a defect. As will be described further with reference to FIG. 2, the computer 36 constructs files comprising records of scanned defects that are then stored in the database 38. Each record includes information concerning the x-location and y-location of the defect, and an estimation of the x-size and y-size of the defect. Other fields of the records include, but are not necessarily limited to, classification codes for the defects.

The review station 42 is used by an operator 46 to manually study defects scanned by the mechanism 40. In a typical conventional application, the operator 46 must study the defects and either enter or modify classification codes into the stored records for the defects on the computer 36.

The tool 14 is capable of generating on its display various graphics indicative of scanned defects. These include histograms, wafer maps, charts or the like. The tool 14 is further capable of assembling files of defect records stored in the database 38 which may then be used to various perform defect analyses. As explained in detail below, the decluster utility 18 is utilized in cooperation with the tool 14 to modify defect records in improvement of subsequent analyses.

The defect analysis system 16 includes a computer 48, a system database 50 and a link 52. The link 52 operatively connects the system 16 to other control systems or computers (not shown) within the fab. In the preferred embodiment, the computer 48 is a commercially available PC or workstation running a Microsoft Windows operating system. Preferably, the system 16 is designed to read defect and sort files in the KLA Results File format, available from KLA instruments Corporation, and also the TLV format, available from Inspex, Inc. The utility 18 is stored in the system 16 as one or more programs for operation on the computer 48 and is preferably written in C++ programming language.

Figure 2:
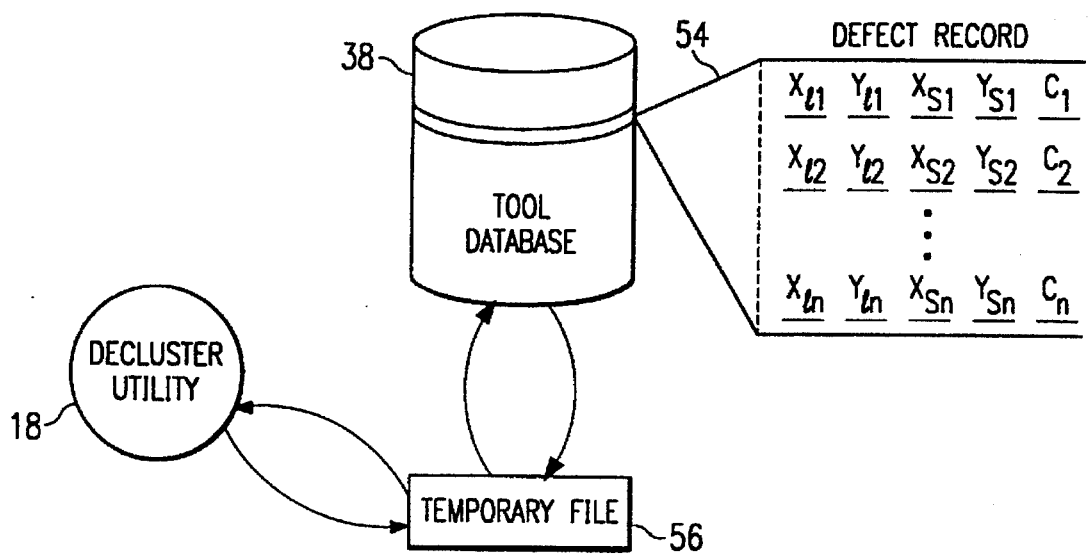
FIG. 2 is a conceptual block diagram of the sequence of operations performed on the defect data by the system of FIG. 1.

FIG. 2 illustrates a general process flow of the sequence of functions performed on defect data in the preferred embodiment of the invention. Referring to both FIGS. 1 and 2, the database 38 of the scan tool 14 is used to store wafer defect data in the form of "records." Shown schematically in FIG. 2 is the data structure of one such record 54 that contains data pertaining to the defects detected on the wafer 32. While not shown, it is understood that multiple records are stored in the database 38, each relating to wafer defects at different reticle layers of wafers in one or more lots. It is appreciated the records are organized into computer files by the computer 36 according to lot, layer and wafer designations, for example.

The record 54 comprises information concerning all of the defects (1 through n) detected on the wafer 32, including the x-location ($X_l$) and y-location ($Y_l$) of each defect, and an estimation of the x-size ($X_s$) and y-size ($Y_s$) of the defect. Another field of the record 54 is classification codes (C) for the defects. The classification codes indicate the nature of the defect and can be used to evaluate whether a defect is critical, i.e., whether it impacts the functionality of the IC. For example, classification codes might classify defects in terms of whether a defect is one that cuts a circuit line, or touches two lines, or whether it is above a particular layer or beneath a particular layer. The classification codes also might classify defects in terms of defect size, i.e., whether it is part of a big cluster or small cluster, or in terms of whether the defect is "discardable" in that it does not represent additional meaningful information for the defect analysis. Other criteria for classification codes are readily understood by those skilled in the art and therefore are not discussed further.

The classification codes for defects in the record 54 are used to make estimates concerning what impact, if any, a particular defect type will have on die or wafer yield. Once the wafer 32 is scanned and the defects are identified in the record 54 in terms of their location data ($X_l$, $Y_l$) and size data ($X_s$, $Y_s$), the normal procedure is then for an operator 46 to review the defects and manually enter the classification codes for each defect into the record 54. This is done by placing the wafer 32 on the review station 42 that includes a microscope (not shown) designed to automatically locate itself to the sites of the defects. The operator 46, based upon judgments about what the defect is, can classify it and then modify the record 54 to include the appropriate classification code.

Wafers can include hundreds of thousands of defects and it is a very time consuming task to manually enter classification codes for each of them in the record 54. Also, some defects do not contribute meaningfully to the data where they all relate to the same cluster of defects, such as scratch. Therefore, before manual review and classification of defects is performed by the operator 46, the decluster utility 18 operates to automatically assign certain classification codes to selected defects in the record 54. In particular, some defects are assigned a classification code indicating they are part of a cluster, i.e., defects in close proximity to one another on the wafer 32, and other defects of the same cluster are assigned a code that indicates them to be "discardable." The discardable defects therefore can be removed from consideration in later classification and yield determining procedures. This procedure is referred to as "declustering" the defect data.

From the database 38, the computer 36 writes out a temporary file 56 that contains the records for a particular lot, such as a lot containing the wafer 32 and its corresponding record 54. The temporary file 56 is stored in the computer 48 of the analysis system 16. The decluster utility 18, running on the computer 48, reads the file 56 and, as explained below, declusters the defect data by entering classification codes into the record 54 to indicate a defect is either part of a cluster or is discardable. With the classification codes thus filled in, i.e., "re-coded" by the utility 18, the modified file 56 is returned to the tool database 38. Typically, the modified file 56 is returned to a different file directory of the tool 14 and then converted to appropriate entries in the database 38.

Accordingly, once the utility 18 has recoded the defect data, the operator 46 can then perform a subsequent manual review of the wafer to further classify defects by concentrating on a much smaller number of them.

Figure 3:
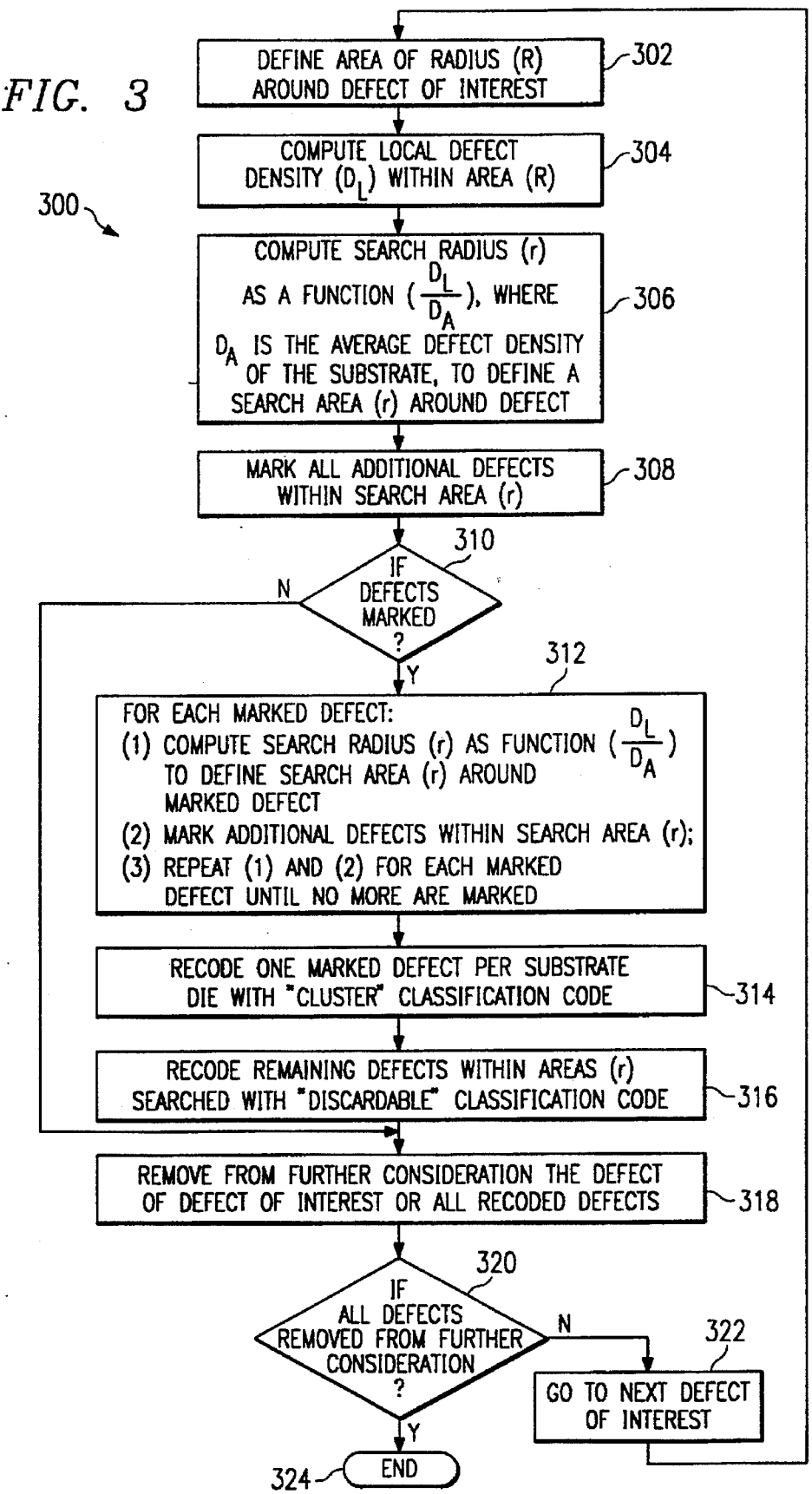
FIG. 3 is a process control flow diagram of the decluster utility of the system of FIG. 1.

FIG. 3 is a process control flow diagram 300 of the decluster utility 18. Generally, in performing the decluster operation the utility 18 determines whether a particular defect is part of a highly concentrated area of defects, i.e., a cluster, by searching an area surrounding the defect to determine if any other defects are found within the same area. Critical to the accuracy of the determination is how the radius of the search area is chosen, given that defect conditions on wafers tend to vary. As explained further below, the search radius for each defect of interest is computed as a function of the ratio of the local defect density ($D_L$) in an area around the defect to the wafer's average defect density ($D_A$). This density ratio function enables the search radius to be small when the density ratio is small, and large when the density ratio is large, within minimum and maximum limits.

Figure 4A:
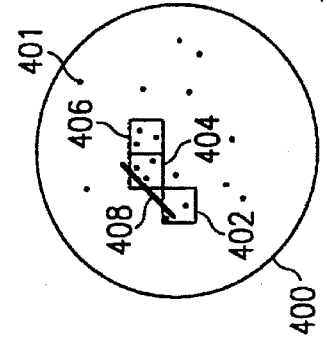
FIG. 4a is a schematic diagram of a wafer substrate containing defects to be analyzed by the system of FIG. 1.
Figure 4B:
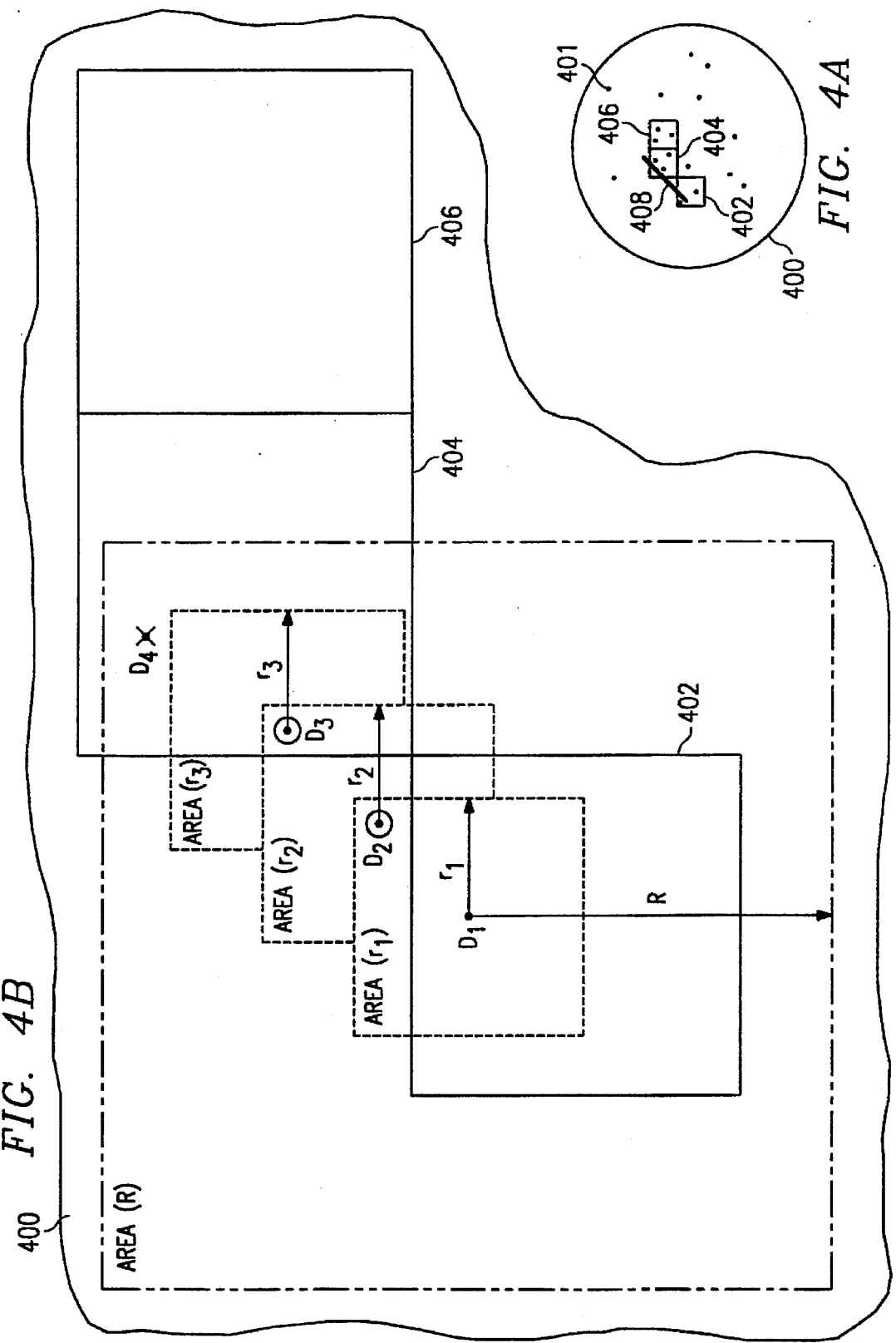

FIGS. 4a and 4b schematically illustrate a wafer substrate 400 for purposes of explaining the operation of the utility 18. The substrate 400 includes a plurality of defects 401 thereon. Dice 402, 404 and 406 are illustrated on the substrate 400, it being understood the substrate includes many other die (not shown). A scratch 408 extends across a large area of the substrate 400 over the regions of dice 402 and 404. The scratch 408 represents a concentrated area of defects forming a big cluster. FIG. 4b is an enlargement of the substrate 400 in the area of the scratch 408, with only defects D1–D4 thereof being shown to demonstrate principles of the invention.

Referring to FIGS. 3 and 4b, the utility 18 performs an iterative recoding process on defect data pertaining to the substrate 400, beginning with a first defect of interest, D1. In step 302 the utility 18 defines an area of radius (R) around the defect of interest. This is shown in FIG. 4b by a box "AREA (R)" drawn around the defect D1. The radius (R) is a parameter set in the utility 18, along with certain other parameters explained more fully below. Typically, the radius (R) is about 5000 microns in length. In step 304 the local defect density ($D_L$) within the AREA (R) is computed. $D_L$ is the number of defects within AREA (R) divided by its area.

In step 306 the search radius (r1) from the defect of interest is computed to define a search area around the defect of interest. The search area is shown in FIG. 4b by the box "AREA (r1)" drawn around the defect D1, for example. The search radius (r1) is computed as a function of the ratio of the local defect density ($D_L$) to the substrate's average defect density ($D_A$) and varies between minimum and maximum limits, as discussed later in detail with reference to FIG. 5.

In step 308 all of the defects (other than the defect of interest) located within the search area are marked. In FIG. 4b for example, the search area defined by AREA (r1) includes both the defect of interest D1 and another defect, D2. Therefore defect D2 is marked as schematically represented in FIG. 4b by it being encircled. In step 310 it is determined whether any defects were marked in step 308. If not, operation proceeds to step 318, discussed below, and otherwise if defects were marked operation proceeds to step 312.

In step 312, several operations are performed for each marked defect. First, a search radius is computed around the marked defect to define a search area around the marked defect. The search radius is computed in the same manner as described above. Second, all defects (other than the already marked defect of interest) located within the defined search area are marked. Third, the process of computing a search radius and defining a search area around each marked defect, and marking additional defects, is repeated until no more defects can be marked.

FIG. 4b illustrates the operation of step 312. Since in step 308 defect D2 was marked in AREA (r1), in step 312 a search radius (r2) is calculated to define a search area "AREA (r2)" around defect D2. Defect D3 is within AREA (r2) and therefore is marked. A search radius (r3) is then calculated to define a search area "AREA (r3)" around defect D3. Since no other defects are found in AREA (r3), step 312 is complete and no additional search areas are defined. In step 314 one marked defect in each die of the substrate is assigned a classification code indicating it to be part of a cluster. In assigning the "cluster" classification code the defect is said to be "recoded" in the sense that the defect record for that defect is modified from what it contained previously. The "cluster" classification code is assigned to one defect in each die even though the defects may be part of the same big cluster, so that each die is self-contained with meaningful information for later analysis purposes. In this manner the utility 18 enables analysis of individual die in addition to analysis of the substrate as a whole.

In the preferred embodiment the "cluster" classification code assigned to the defect in step 314 differentiates between "small" and "big" clusters. Either a "small cluster" code or a "large cluster" code is assigned, based upon the number of marked defects within the die. For example, a "large cluster" code might be assigned where there are 4 or more marked defects on the die from which the one defect to be assigned the cluster code is chosen. Other parameters may be selected to differentiate between small and big clusters.

In step 316 the remaining defects within all of the search areas are assigned a "discardable" classification code. The remaining defects are thus recoded as discardable because they do not necessarily need to be considered in a subsequent analysis. They are duplicative of the information already available from the cluster code designations. In this sense, by classifying some defects of a cluster as part of the cluster and classifying the remaining defects of the cluster as discardable, the defect data is said to be "declustered."

In step 318 defects that are within a search area are removed from further consideration in subsequent iterations of the marking and recoding process performed by the utility 18. Specifically, if no defects had been marked within the initial search area as determined in step 308, execution proceeds to step 318 wherein the defect of interest within that search area is removed from subsequent consideration. If defects had been recoded in steps 312–316 as being either part of a cluster or as discardable, then in step 318 those defects are removed from further consideration.

In step 320 a determination is made whether all of the defects on the substrate have been removed from further consideration, either because they were a searched defect of interest or were recoded, as explained above. If all defects are not yet removed from consideration, in step 322 the next defect of interest is identified and execution returns to step 302 so that the analysis can be repeated. Otherwise, operation ends in step 324. It is appreciated that when the analysis is performed for the next defect of interest following step 322, the search radius will differ if the local defect density ($D_L$) surrounding that defect has changed. Accordingly, the search radius changes with conditions on the wafer, for reasons described fully below.

Steps 314–324 are further explained with reference to FIG. 4b. In step 314, one marked defect is recoded with a "cluster" classification in each of the dice 402 and 404, and in step 316 the remaining defects within the searched areas (both marked defects and examined defects of interest) are recoded as discardable. For example, defect D2 in die 402 and defect D3 in die 404 are recoded "cluster" and the remaining defect, D1, is recoded "discardable." In step 322, the next defect of interest to be analyzed would be defect D4, because it has not yet been removed from consideration. Steps 302–324 are then repeated for defect D4.

Figure 5:
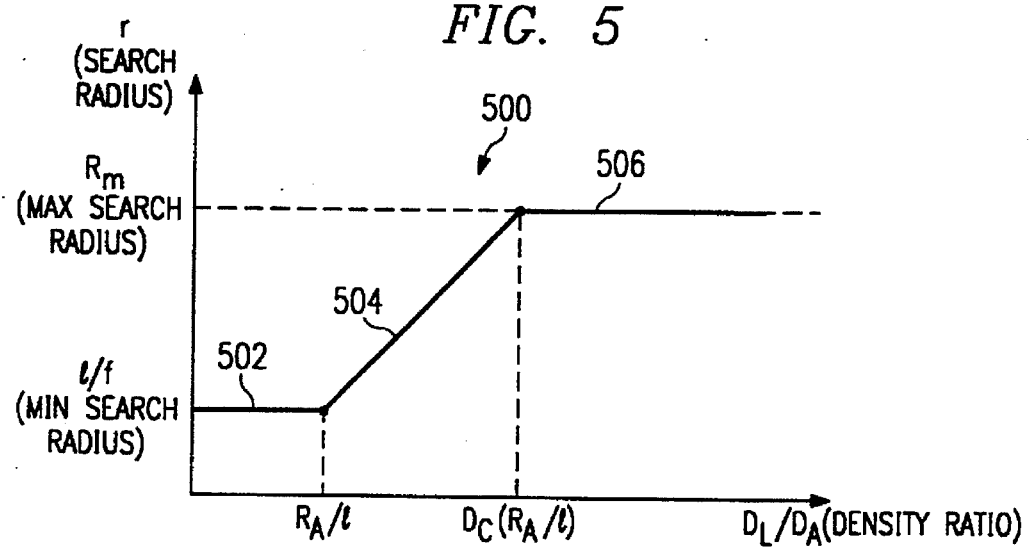
FIG. 5 is a graphical representation of the relationship between defect search radius (r) and density ratio ($D_L/D_A$) implemented by the decluster utility.

FIG. 5 illustrates a graph 500 of the relationship between the search radius (r) and the defect density ratio ($D_L/D_A$), as determined by the utility 18 in step 306 of FIG. 3. In the preferred embodiment, the search radius (r) shown in the graph 500 is calculated by the following equations:

$$r = l/f \text{ if } D_L/D_A \leq R_A/l \quad (1)$$

$$r = l/f + \left( \frac{R_M - l/f}{(R_A/l)(D_C) - R_A/l} \right) \text{ if } R_A/l \leq D_L/D_A \leq D_L(R_A/l) \quad (2)$$

$$r = R_M \text{ if } D_L/D_A \geq D_C(R_A/l) \quad (3)$$

where $D_C$ is a density cutoff parameter; $R_M$ is a maximum search radius parameter; f is a density divider parameter; $R_A$ is a density average radius parameter; N is the total number of defects detected on the substrate; A is the area of the substrate; $D_a$ is the wafer average density (i.e., $D_A=(N/A)$); l is the mean distance between randomly distributed defects on the substrate (i.e., $l = \text{sqrt}(A/N) = (1/(\text{sqrt}(D_A)))$; and $D_L$ is the local defect density computed for each defect as described above in step 302. In the preferred embodiment, the density cutoff parameter ($D_C$) is set to about 10, although may range between 5 and 20. The maximum search radius ($R_M$) is set to about 3000 microns. The density divider parameter (f) is set to about 16, although may range from about 10 to 20. The density average radius ($R_A$) is set to about 5000 microns. These parameters are set empirically and may further vary according to wafer conditions.

Equation (1) describes a first region 502 of the graph 500 where the search radius (r) is set at a constant minimum value (l/f), for density ratios ($D_L/D_A$) of less than $R_A/l$. Thus when the parameter f is set at 16, the minimum radius is equal to a fraction (i.e., 1/16) of the mean distance between randomly distributed defects (f) on the wafer. In region 502 the density ratio is low because the local defect density ($D_L$) is close to the average defect density ($D_A$). Choosing a relatively low minimum search radius (l/f) prevents two closely spaced defects from being treated together as one cluster when in fact they are not. However, as the local defect density ($D_L$) increases (as does the density ratio $D_L/D_A$), it is expected a cluster such as that formed by a scratch must be present, so the search radius ought to be expanded to include additional defects. This is accomplished in the second region 504 of the graph.

Equation (2) describes the second region 504 of the graph where the search radius linearly increases as the density ratio ($D_L/D_A$) increases. As the local density increases, the radius is expanded to capture additional defects as part of the same cluster. The larger radius as accounts for possible gaps in a single cluster as improperly causing the utility 18 to treat the cluster as separate clusters. The radius increases gradually because if the radius were instead always at a fixed maximum value, it would include too many defects in one cluster in places where defect density is relatively low.

Equation (3) describes the third region 506 of the graph 500 where the search radius (r) is set at the maximum search radius ($R_M$) value. When the density ratio ($D_L/D_A$) becomes very high, beyond $D_C(R_A/1)$, the search radius (r) must be fixed so that it will not become so large as to capture multiple clusters or treat the entire wafer as a single cluster.

Several advantages result from the way the search radius is computed by the utility 18. Varying the search radius as a function of the ratio of the local defect density ($D_L$) to the wafer's average defect density ($D_A$) accounts for differing conditions that occur on wafers. On a densely defective wafer, the presence of multiple clusters are more accurately recognized instead of being treated as one all-encompassing cluster. Also, single clusters, such as those caused by a scratch, are more accurately recognized as one cluster instead of being treated as several clusters having small gaps therebetween. Further, by assigning cluster designations to individual die, analysis is more readily performed on a per-die basis instead of only at the wafer level.

Figure 6A:
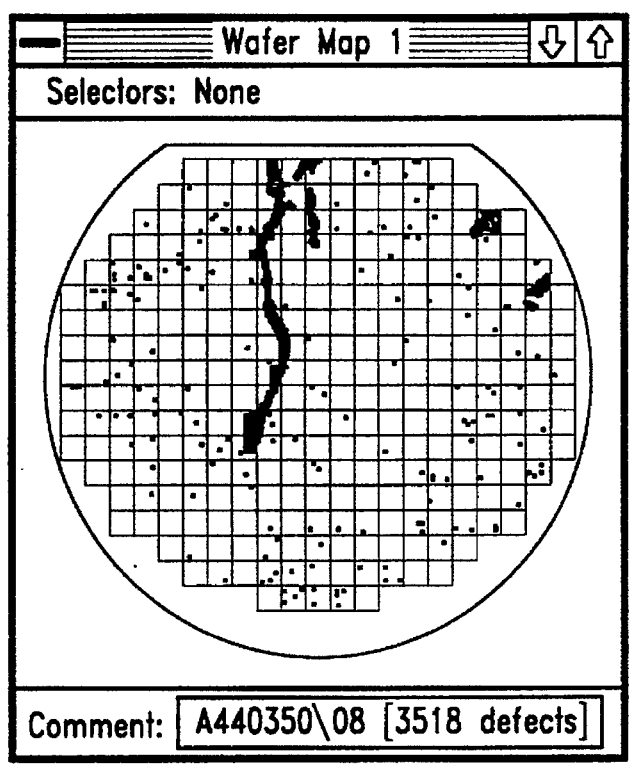
FIGS. 6a–6f are displays illustrating wafer maps and a defect type pare to for an example defect record.
Figure 6B:
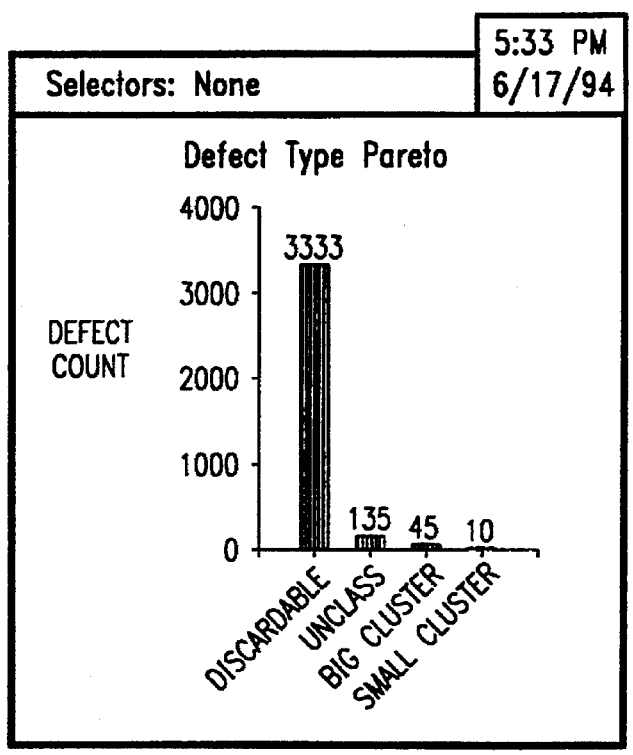
Figure 6C:
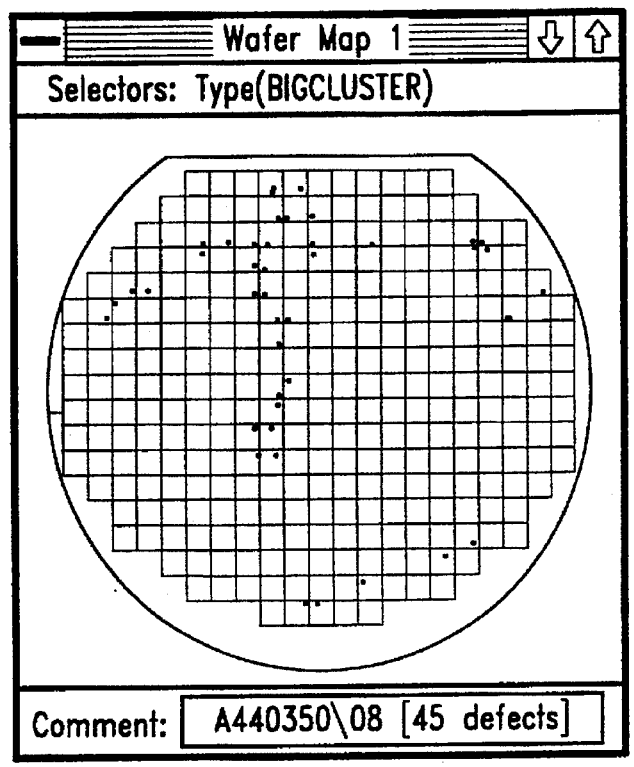
Figure 6D:
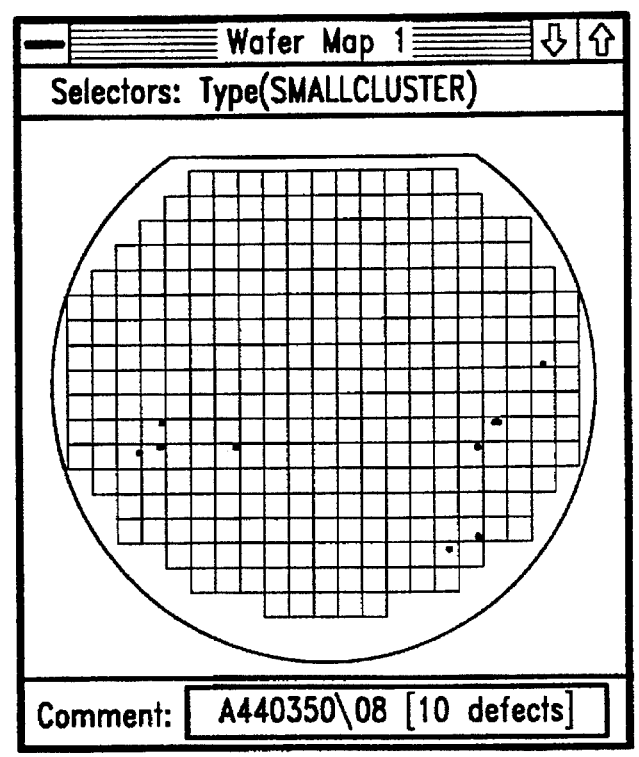
Figure 6E:
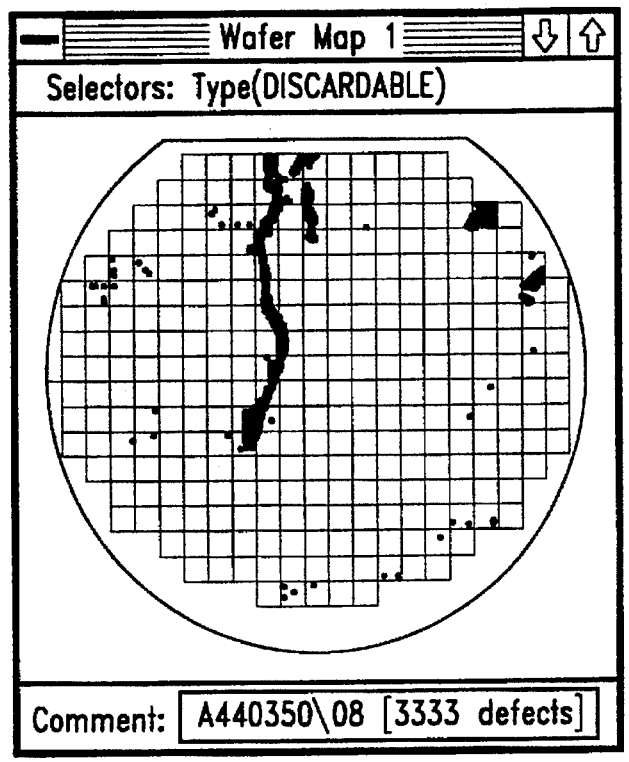
Figure 6F:
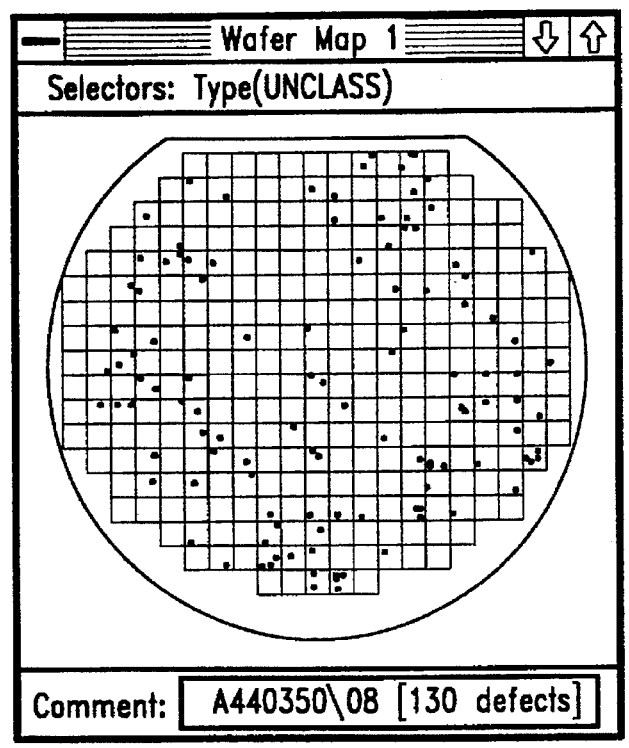

FIGS. 6a–6f are displays illustrating wafer maps and a defect type pareto (FIG. 6b) for an example defect record processed by the utility 18. In FIG. 6a, a wafer map 600 is shown for a defect record "A440350/8." The map 600 shows 3518 defects, many of which are concentrated in a scratch across the wafer. FIG. 6b is a defect type pareto showing the breakdown of defects as determined by the utility 18. Specifically, out of the 3518 defects, 3333 are discardable, 130 are unclassifiable, 45 are big clusters and 10 are small clusters. FIG. 6c–6f are wafer maps 602, 604, 606, 608 showing the big clusters, small clusters, discardable, and unclassifiable defects, respectively.

It is understood that the present invention can take many forms and embodiments. The embodiments shown herein are intended to illustrate rather than to limit the invention, it being appreciated that variations may be made without departing from the spirit of the scope of the invention. For example, the decluster utility may comprise one or more computer programs operable on either the system 16 or on the tool 14, such that a computer separate from the scan tool may not necessarily be required. The utility may be used to classify codes other than decluster and discardable codes and examine points on a substrate other than defects. Substrates other than wafers may be examined. The area (R) or search area (r) may be defined as a circle, box or other geometric shape. The utility may be implemented in any appropriate programming language and run in cooperation with any computer system or scan tool.

Although illustrative embodiments of the invention have been shown and described, a wide range of modification, change and substitution is intended in the foregoing disclosure and in some instances some features of the present invention may be employed without a corresponding use of the other features. Accordingly, it is appropriate that the appended claims be construed broadly and in a manner consistent with the scope of the invention.

What is claimed is:

1. A method for assigning classification codes to data associated with points on a substrate, the method comprising:

determining the local density of said points within a preselected area of said substrate and determining the average density of all of said points on said substrate;

defining a search area around one of said points, said search area having a radius proportional to the ratio of said local density to said average density;

marking said points within said search area, and for each said marked point, defining a new search area around said marked point, said new search area having a radius proportional to the ratio of said local density to said average density, marking additional said points within said new search area, and repeating said new search area defining and said additional point marking until no further ones of said points are marked; and assigning at least one of said marked points with a first classification code and assigning the remaining said points within said search area and said new search areas with a second classification code.

2. The method of claim 1 wherein said radius of said search area is set at a minimum radius for said density ratios of less than a preselected value.

3. The method of claim 1 wherein said radius of said search area linearly increases as said density ratio increases.

4. The method of claim 1 wherein said radius of said search area is set at a maximum radius for said density ratios of greater than a preselected value.

5. The method of claim 1 wherein said substrate has multiple dice and said step of assigning said first classification code comprises assigning said marked points on separate ones of said dice each with said first classification code.

6. The method of claim 1 wherein said first classification code is a cluster classification code.

7. The method of claim 1 wherein said second classification code is a discardable classification code.

8. The method of claim 6 wherein said cluster classification code is a big cluster classification code when the number of said assigned second classification codes exceeds a preselected number and otherwise said cluster classification code is a small cluster classification code.

9. The method of claim 1 wherein said points comprise defects on said substrate.

10. A method for assigning classification codes to data associated with points on a substrate, the method comprising the steps of:

(a) determining the local density of said points within a preselected area of said substrate and determining the average density of all of said points on said substrate;

(b) defining a search area around one of said points, said search area having a radius proportional to the ratio of said local density to said average density;

(c) marking said points within said search area, and for each said marked point, defining a new search area around said marked point, said new search area having a radius proportional to the ratio of said local density to said average density, marking additional said points within said new search area, and repeating said new search area defining and said additional point marking until no further ones of said points are marked;

(d) assigning at least one of said marked points with a first classification code and assigning the remaining said points within said search area and said new search areas with a second classification code;

(e) removing from further analysis said point of interest if no said points are marked within said search area and otherwise removing from further analysis said code-assigned points; and (f) identifying a point of interest of said points that has not been removed from further analysis and repeating steps (a)–(e) until all said points are removed.

11. The method of claim 10 wherein said radius of said search area is set at a constant minimum value (l/f), for said density ratios of less than $R_A/l$.

12. The method of claim 10 wherein said radius of said search area linearly increases as said density ratio increases for said density ratios greater than $R_A/l$ and less than $D_C(R_A/l)$.

13. The method of claim 10 wherein said radius of said search area is set at a maximum radius for said density ratios of greater than $D_C(R_A/l)$.

14. The method of claim 10 wherein said substrate has multiple dice and said step of assigning said first classification code comprises assigning said marked points on separate ones of said dice each with said first classification code.

15. The method of claim 10 wherein said first classification code is a cluster classification code and said second classification code is a discardable classification code.

16. A computer program for assigning classification codes to data associated with points on a substrate, the program stored on a computer-readable medium, comprising:
  instructions for determining the local density of said points within a preselected area of said substrate and determining the average density of all of said points on said substrate;
  instructions for defining a search area around one of said points, said search area having a radius proportional to the ratio of said local density to said average density;
  instructions for marking said points within said search area, and for each said marked point, defining a new search area around said marked point, said new search area having a radius proportional to the ratio of said local density to said average density, marking additional said points within said new search area, and repeating said new search area defining and said additional point marking until no further ones of said points are marked; and
  instructions for assigning at least one of said marked points with a first classification code and assigning the remaining said points within said search area and said new search areas with a second classification code.

17. The program of claim 16 wherein said radius of said search area is set at a minimum radius for said density ratios of less than a preselected value.

18. The program of claim 16 wherein said radius of said search area linearly increases as said density ratio increases.

19. The program of claim 16 wherein said radius of said search area is set at a maximum radius for said density ratios of greater than a preselected value.

20. The program of claim 16 wherein said substrate has multiple dice and said step of assigning said first classification code comprises assigning said marked points on separate ones of said dice each with said first classification code.

21. The program of claim 16 wherein said first classification code is a cluster classification code.

22. The program of claim 16 wherein said second classification code is a discardable classification code.

23. The program of claim 21 wherein said cluster classification code is a big cluster classification code when the number of said assigned second classification codes exceeds a preselected number and otherwise said cluster classification code is a small cluster classification code.

24. Apparatus for assigning classification codes to data associated with points on a substrate, the apparatus comprising:
  means for determining the local density of said points within a preselected area of said substrate and determining the average density of all of said points on said substrate;
  means for defining a search area around one of said points, said search area having a radius proportional to the ratio of said local density to said average density;
  means for marking said points within said search area, and for each said marked point, defining a new search area around said marked point, said new search area having a radius proportional to the ratio of said local density to said average density, marking additional said points within said new search area, and repeating said new search area defining and said additional point marking until no further ones of said points are marked; and
  means for assigning at least one of said marked points with a first classification code and assigning the remaining said points within said search area and said new search areas with a second classification code.

25. The apparatus of claim 24 wherein said radius of said search area is set at a constant minimum value (l/f), for said density ratios of less than $R_A/l$.

26. The apparatus of claim 24 wherein said radius of said search area linearly increases as said density ratio increases for said density ratios greater than $R_A/l$ and less than $D_C(R_A/l)$.

27. The apparatus of claim 24 wherein said radius of said search area is set at a maximum radius for said density ratios of greater than $D_C(R_A/l)$.

28. The apparatus of claim 24 wherein said substrate has multiple dice and said step of assigning said first classification code comprises assigning said marked points on separate ones of said dice each with said first classification code.

29. Apparatus for assigning classification codes to data associated with defects on a substrate, the apparatus comprising:
  means for determining the local density of said defects within a preselected area of said substrate and determining the average density of all of said defects on said substrate;
  means for defining a search area around at least one of said defects, said search area having a radius proportional to the ratio of said local density to said average density;
  means for marking said defects within said search area, and for each said marked point, defining a new search area around said marked point, said new search area having a radius proportional to the ratio of said local density to said average density, marking additional said defects within said new search area, and repeating said new search area defining and said additional defect marking until no further ones of said defects are marked; and
  means for assigning at least one of said marked defects with a first classification code and assigning the remaining said defects within said search area and said new search areas with a second classification code.

30. A method for selecting the radius of a search area for defects to be marked in assigning classification codes to defect data pertaining to a substrate, the method comprising:
  determining the local density of said defects within a preselected area of said substrate;
  determining the average density of all of said defects on said substrate;
  and defining said search radius to be proportional to the ratio of said local density to said average density.

31. The method of claim 30 wherein said search radius is set at a minimum radius for said density ratios of less than a preselected value.

32. The method of claim 30 wherein said search radius linearly increases as said density ratio increases.

33. The method of claim 30 wherein said search radius is set at a maximum radius for said density ratios of greater than a preselected value.

* * * * *

UNITED STATES PATENT AND TRADEMARK OFFICE
CERTIFICATE OF CORRECTION

PATENT NO.    : 5,649,169
DATED         : July 15, 1997
INVENTOR(S)   : Berezin et al.

It is certified that error appears in the above-identified patent and that said Letters Patent is hereby corrected as shown below:

Title page,
Item [56], References Cited, OTHER PUBLICATIONS, in the title of the second listed reference, "Enchancement" should read -- Enhancement --.

Column 1,
Line 9, "spacial" should read -- spatial --.

Column 3,
Line 2, after "codes", please delete -- are --.
Line 37, "pare to" should read -- pareto --.

Column 4,
Line 32, "microscopeto" should read -- microscope to --.
Line 58, "various" should read -- variously --.

Column 5,
Line 4, "instruments" should read -- Instruments --.

Signed and Sealed this

Twelfth Day of November, 2002

Attest:

JAMES E. ROGAN
Attesting Officer      Director of the United States Patent and Trademark Office